(12) United States Patent
Josimovic-Alasevic et al.

(10) Patent No.: US 8,148,150 B2
(45) Date of Patent: Apr. 3, 2012

(54) METHOD FOR THE PRODUCTION OF INTERVERTEBRAL DISK CELL TRANSPLANTS AND THEIR USE AS TRANSPLANTATION MATERIAL

(75) Inventors: Olivera Josimovic-Alasevic, Berlin (DE); Jeanette Libera, Berlin (DE); Vilma Siodla, Kleinmachnow (DE); Hans-Joerg Meisel, Berlin (DE)

(73) Assignee: CO.DON AG, Teltow (DE)

( * ) Notice: Subject to any disclaimer, the term of this patent is extended or adjusted under 35 U.S.C. 154(b) by 940 days.

(21) Appl. No.: 10/596,357

(22) PCT Filed: Dec. 13, 2004

(86) PCT No.: PCT/DE2004/002761
§ 371 (c)(1), (2), (4) Date: Jun. 12, 2008

(87) PCT Pub. No.: WO2005/055877
PCT Pub. Date: Jun. 23, 2005

(65) Prior Publication Data
US 2008/0249624 A1 Oct. 9, 2008

Related U.S. Application Data

(60) Provisional application No. 60/544,315, filed on Feb. 17, 2004.

(30) Foreign Application Priority Data

Dec. 12, 2003 (DE) .................................. 103 59 830
Sep. 6, 2004 (DE) ......................... 10 2004 043 449

(51) Int. Cl.
*C12N 5/00* (2006.01)

(52) U.S. Cl. ....... 435/373; 435/325; 435/347; 424/93.1; 424/93.7

(58) Field of Classification Search .................. 435/325, 435/347, 373; 424/93.1, 93.7
See application file for complete search history.

(56) References Cited

U.S. PATENT DOCUMENTS

2003/0153078 A1 * 8/2003 Libera et al. .................. 435/383
2003/0165473 A1 * 9/2003 Masuda et al. ............... 424/93.7
2003/0229400 A1 * 12/2003 Masuda et al. ............. 623/23.63

FOREIGN PATENT DOCUMENTS

WO    WO 0168811 A2 * 9/2001

OTHER PUBLICATIONS

J.A. Reinecke, et al.; "In vitro Transfer von Genen in spinale Gewebe"; Z. Orthop., 1997, vol. 135, pp. 412-416.
Masahiko Okuma, et al.; "Reinsertion of Stimulated Nucleus Pulposus Cells Retards Intervertebral Disc Degeneration: An In Vitro and In Vivo Experimental Study"; Journal of Orthopaedic Research; The Journal of Bone and Joint Surgery, Inc.; vol. 18, No. 6, pp. 986-997, 2000.

* cited by examiner

*Primary Examiner* — Taeyoon Kim
(74) *Attorney, Agent, or Firm* — Norris McLaughlin & Marcus, P.A.

(57) ABSTRACT

The invention relates to a method for the in vitro production of intervertebral disk cartilage cell transplants from affected intervertebral disk tissue from patients and to the use thereof as transplantation material for the treatment of affected intervertebral disks. The invention also relates to a three-dimensional, vital, and mechanically stable intervertebral disk cartilage tissue and to the use thereof as transplantation material for the treatment of affected intervertebral disks and in testing active substances. Furthermore, the invention is directed to the surgical technique for incorporating the transplants, to the intervertebral disk cell transplants and intervertebral disk cartilage tissues produced, and to therapeutic formulations, e.g. injection solutions, which include said tissue and said cell transplants.

5 Claims, 5 Drawing Sheets

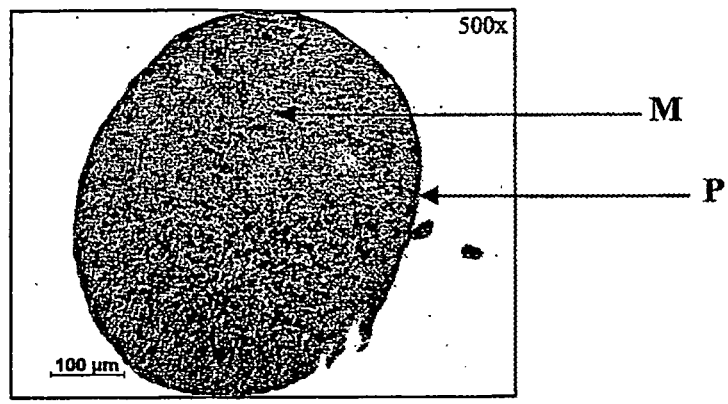
Fig. 1: Histology of *in vitro*-produced, three-dimensional intervertebral disk cartilage tissues. Vital differentiated cells having developed an extracellular matrix (ECM) are situated inside the tissues. A proliferation zone (P) is situated at the periphery.

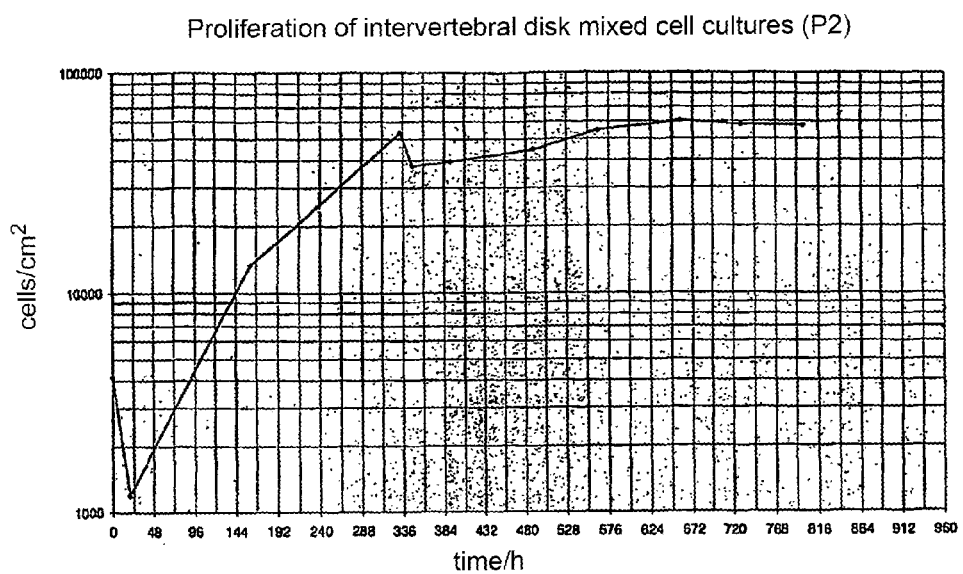
Fig.2: Proliferation of intervertebral disk cells in mixed culture in the monolayer passage 2.

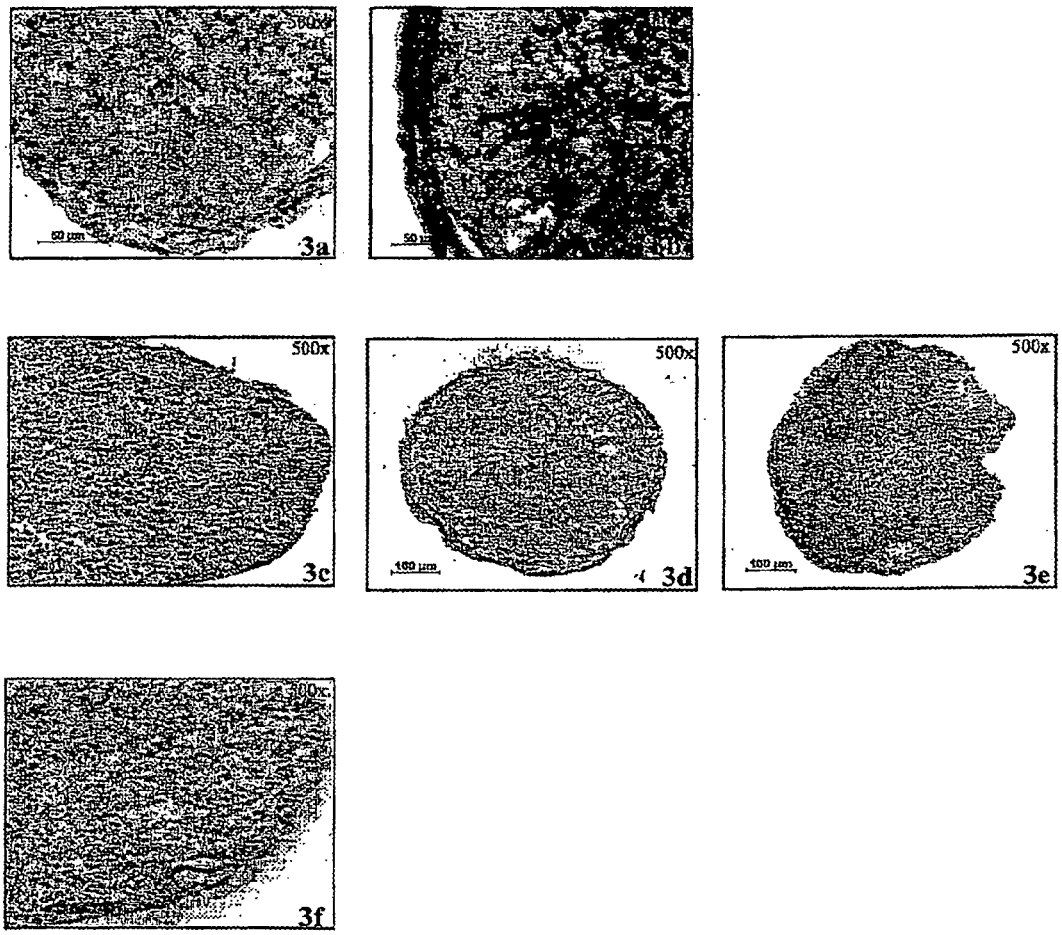

Fig. 3: Expression of matrix proteins by intervertebral disk cartilage mixed cells following growth in monolayer culture and subsequent culturing under three-dimensional cell culturing conditions. (3a) Expression of aggregan after 4 weeks. (3b) Expression of hyalin-specific proteoglycans detected by means of Safranin O staining after 4 weeks. (3c) Expression of type I collagen after 2 weeks. (3d) Expression of type II collagen after 4 weeks. (3e) Expression of type III collagen after 4 weeks.

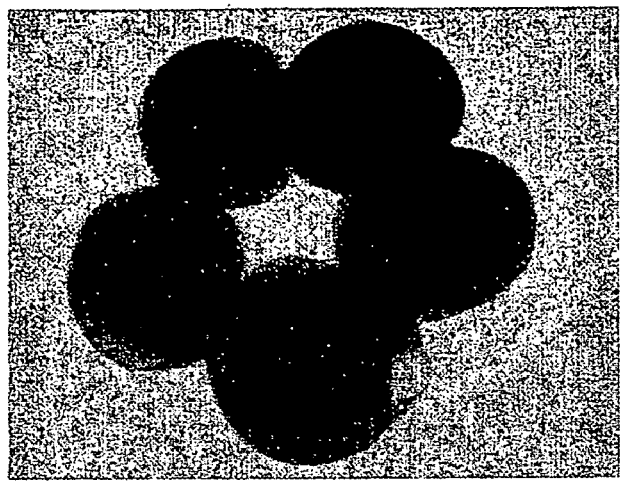
Fig. 4: Five fusing three-dimensional intervertebral disk cartilage tissues.

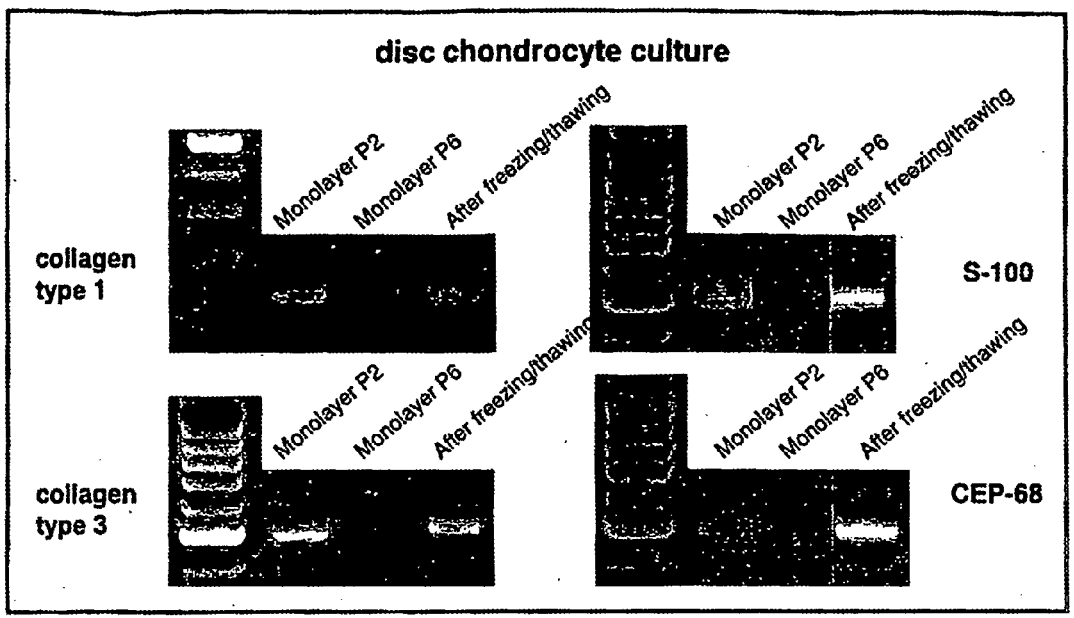
Fig. 5: Expression of different matrix and regulative proteins by disc derived chondrocytes cultured in monolayer for different passages and cultured in monolayer after freezing and thawing of cells. Monolayer passage 2 (P2), Monolayer passage 6 (P6), after freezing and thawing (after freezing/thawing).

METHOD FOR THE PRODUCTION OF INTERVERTEBRAL DISK CELL TRANSPLANTS AND THEIR USE AS TRANSPLANTATION MATERIAL

The invention relates to a method for the in vitro production of intervertebral disk cartilage cell transplants from affected intervertebral disk tissue from patients and to the use thereof as transplantation material for the treatment of affected intervertebral disks. The invention also relates to a three-dimensional, vital, and mechanically stable intervertebral disk cartilage tissue and to the use thereof as transplantation material for the treatment of affected intervertebral disks and in testing active substances. Furthermore, the invention is directed to the intervertebral disk cell transplants produced, the transplantation technology, and the intervertebral disk cartilage tissues produced, and to therapeutic formulations, e.g. injection solutions containing said tissue and cell transplants.

Degeneration of intervertebral disks is initiated during ageing or as a result of traumas, inducing acute and chronic pain and instabilities in the vertebral column. More than 300,000 patients in Europe are suffering from a discopathy. Approximately 70% of the patients suffering from a prolapsed intervertebral disk and being treated by means of discectomy are still suffering from pain in their backs. In 10% of these patients, persistent severe pain necessitates further surgical treatment (Yorimitsu et al., 2001). This is due to a reduced height of the intervertebral disk as a result of surgery, an increase of local strain on the intervertebral disk tissue associated therewith (Brinckmann and Grootenboer, 1991), and, in particular, lack of healing and regeneration of destroyed and removed intervertebral disk tissue (Lundon and Bolton, 2001; Meakin et al., 2001). In the course of time, the instability of the affected intervertebral disk results in degenerative changes of adjoining intervertebral disks, thereby necessitating further surgical intervention and, in the worst case, fusion of vertebral bodies or insertion of a prosthesis. Therefore, biological repair or regeneration of intervertebral disks represents the future in treating degenerate intervertebral disks.

A well-known method for the biological regeneration of tissue is cartilage cell transplantation using autologous cells, which method has been used in the treatment of joint cartilage defects. This method utilizes the potential of joint cartilage cells of building up new tissue in vivo after transplanting the cells. To this end, a joint cartilage biopsy is taken from the patient, cartilage cells are isolated therefrom, grown by means of cell culturing, and transplanted into the patient in the area of the tissue defect e.g. by injection. There, they form new tissue, thus completely filling up the defect. This method achieves formation of tissue in the body after application of a cell transplant. In principle, this methodology cannot be used in the treatment of intervertebral disk degeneration because extraction of starting material from an intact adjacent intervertebral disk of a patient is not possible for ethical reasons and affected tissue cannot be used a priori.

Initial approaches to biological replacement of intervertebral disks have been using healthy intervertebral disk tissue as starting material. Thus, Handley (U.S. Pat. No. 6,080,579) and Ferree (U.S. Pat. No. 6,340,369 B1) describe the use of normal intervertebral disk tissue to isolate intervertebral disk cells and combine these cells with a bioabsorbable carrier. Similarly, a great deal of scientific work is based on the use of normal intervertebral disk tissue: Okuma et al., 2000, Gruber et al., 2000, Chelberg et al., 1995. However, a healthy intervertebral disk of a patient cannot be used as a source of tissue to treat another intervertebral disk because removal of tissue results in destruction, degeneration and, as a consequence, loss of function of this intervertebral disk.

Another approach involves the use of degenerate nucleus pulposus tissue which is removed from the inside of a degenerate intervertebral disk and worked up. This surgical intervention further destroys the intervertebral disk which is degenerated and destroyed anyway. On the one hand, work-up of the tissue is suggested to be dehydration (U.S. Pat. No. 6,648,918) or combination of cells present therein with a carrier material (U.S. Pat. No. 6,569,442; US 2001/0020476 A1) and subsequent re-transplantation into the degenerate intervertebral disks. However, the dehydrated tissue does not include any living cells and consequently does not represent a method of biological re-generation. The suggested combination of nucleus cells or other cells with a carrier material neither represents a purely biological method and calls for the use of a suitable carrier material which, for example, must be suitable in biomechanical terms, which is to be formed and is degraded in the same way as new tissue, which must not impair the formation of new tissue or, for example, trigger immunologic reactions due to synthetic, allogenic or xenogenic materials used in any event.

Another option of treatment involves the use of intervertebral disks from other patients, which would therefore be an allogenic transplantation (U.S. Pat. No. 6,344,058; Keith DK et al., 2003). In this event, however, immunologic reactions represent a problem, and mere introduction of a donor intervertebral disk would probably not induce any biological regeneration of the affected intervertebral disk. As a consequence of the problems mentioned above, the general targets in treating degenerate intervertebral disks and regenerating intervertebral disks are therefore as follows: using medically and ethically justifiable starting tissue or cell samples, avoiding destruction of other intervertebral disks or of the affected, diseased intervertebral disk of a patient, using materials from the patient only (autologous therapy), finding optimum conditions of cell isolation and culturing for the growth of intervertebral disk cells and subsequent formation of intervertebral disk matrix, doing without carrier materials so as to avoid immune reactions. The above problems can be solved by transplanting a specific autologous cell transplant or by transplanting a three-dimensional intervertebral disk cartilage tissue which has been prefabricated outside the body.

The object of the present invention was therefore to provide methods for the production of intervertebral disk cartilage cell transplants and stable vital intervertebral disk cartilage tissue suitable for autologous transplantation, rapid re-development and conservation of the intervertebral disk function. It is essential that the starting material for the production of the cell transplants can be collected in a medically and ethically justifiable manner, and that the intervertebral disk cells cultured in an autologous fashion do not undergo changes over the time period from collection to transplantation and have high proliferation and differentiation capacities.

Surprisingly, it was possible to demonstrate that affected intervertebral disk tissue can be used as starting material. Up to now, it has been assumed that degenerate tissue could not be used to isolate adult cells in sufficient number, which cells would be vital, have sufficient proliferation, and subsequently be even capable of differentiating in a tissue-specific manner to form intervertebral disk tissue, because tissue-specific cells in tissues subject to degeneration change their properties with respect to matrix synthesis, being destroyed and even replaced by other cells with different properties lacking tissue specificity. Surprisingly, however, it was possible to isolate a sufficient number of vital cells particularly from prolapsed degenerate intervertebral disk tissue. Such prolapsed degenerate intervertebral disk tissue consists of intervertebral disk portions of the fibrous ring and of the pulpy nucleus, and the cells isolated from the above two tissue areas (anulus fibrosus cells and nucleus pulposus cells) even proliferate and differentiate tissue-specifically in a particularly specific manner under the autologous culturing conditions that are present. Hence, the above mixed-cell transplants are suitable for a cell-based therapy to restore the function of an intervertebral disk.

Thus, a method is described for the first time which allows production of specific autologous mixed-cell intervertebral disk transplants which, following transplantation in a damaged/affected intervertebral disk, can save the intervertebral disk by forming new intervertebral disk tissue and, as a consequence, restore the neurological and mechanical functions of the vertebral column in cases of discopathy or prolapsed intervertebral disk.

Even in advanced degeneration of an intervertebral disk, i.e., degeneration or traumatic lesion of the outer layer of the intervertebral disk (anulus fibrosus), the present invention permits restoration and conservation of the neurological, biological and mechanical functions of the intervertebral disk by isolating mixed tissue cells from prolapsed, degenerate intervertebral disks, which cells are subsequently cultured to form autologous three-dimensional tissue without using carrier materials. The isolated intervertebral disk tissue, especially the intervertebral disk cells, are grown in a cell culture medium preferably under autologous culturing conditions, adding serum from the patient only. During growth, the intervertebral disk cells isolated from degenerate, prolapsed intervertebral disk tissue are preferably cultured in a cell culture medium including 1-20% of added autologous serum, wherein the ratio of alpha-MEM medium and HAM-F12 medium is between 2:1 and 1:2, at 36.8-37° C. in air containing 5% carbon dioxide and having a humidity of 85-95%, the synthesis of matrix and marker proteins by said cells remaining unchanged.

In a likewise preferred fashion the isolated intervertebral disk cells, following growth thereof in monolayer, are cultured in a cell culture medium including 1-20% of added autologous serum, wherein the ratio of alpha-MEM medium and HAM-F12 medium is between 2:1 and 1:2, at 36.8-37° C. in air containing 5% carbon dioxide and having a humidity of 85-95%, thereby becoming capable of differentiating, forming matrix structures comprising specific intervertebral disk matrix proteins.

In a likewise preferred fashion the isolated intervertebral disk cells, following growth thereof in monolayer, are frozen in a solution of 10% DMSO, 20% serum and 70% culture medium, followed by thawing, so that their properties with respect to the synthesis of specific matrix components and markers remain unchanged and tissue structures consisting of intervertebral disk-specific matrix proteins are formed in vitro and in vivo.

The above-described features of unchanged synthesis of marker and matrix proteins do not represent an object or desired function to be achieved, but rather a consequence of the culturing steps. The above features are mentioned merely for reasons of clarification. Accordingly, the disclosure of these features is intended to illuminate the consequences of the inventive steps of use or processing.

Therefore, the formation of matrix structures comprising specific intervertebral disk matrix proteins is not a preferred property; rather, the formation of the above-mentioned matrix structures is a result of the culturing conditions.

In a preferred fashion the cells isolated from intervertebral disk tissue are cultured in a culture vessel with hydrophobic surface and tapering bottom, thereby obtaining three-dimensional cell aggregates.

BRIEF DESCRIPTION OF THE DRAWINGS

FIG. 1 shows the histology of in vitro-produced three-dimensional intervertebral disk cartilage tissues in the cross-section of a microscopic image. Vital differentiated cells with extracellular matrix is surrounded by a peripheral proliferation zone P.

FIG. 2 shows the proliferation and high proliferation capacity of intervertebral disk cells in mixed culture (anulus fibrosus and nucleus pulposus) in the monolayer passage 2 (P2). The number of cells per surface area over time is indicated in the graph.

FIG. 3 shows the expression of disk-specific matrix proteins and marker proteins by intervertebral disk cartilage mixed cells following growth in monolayer culture and subsequent culturing under three-dimensional cell culturing conditions. Expression of components of native intervertebral disk cartilage in vivo representing the most important structural proteins crucial for intervertebral disk cartilage function are shown, including matrix and regulatory proteins (aggregan, hyaline-specific proteoglycans, and type I, II and III collagens).

FIG. 4 shows the fusing of five three-dimensional intervertebral disk cartilage tissues during continued culture to achieve larger transplants. The tissue spheres adhere to each other and coalesce as shown, to undergo complete fusion after prolonged culture.

FIG. 5 shows the expression of various matrix and regulative proteins by disc derived chondrocytes cultured in monolayer for different passages of cell culture (P2, P6) and after freezing and thawing, showing that formation of matrix and regulative proteins can be retained.

In treatment using the intervertebral disk cell transplants according to the invention, the outer envelope of the intervertebral disk, i.e., the anulus fibrosus which has been damaged by effusion of intervertebral disk tissue, advantageously heals—prior to transplantation—in such a way that liquids, e.g. the cell transplants produced, could not effuse from the interior of the intervertebral disk. This time period is patient-dependent. The intervertebral disk cell transplants are produced during this period of time, and while growing in the cell culture, the intervertebral disk mixed-cells receive their tissue-specific properties with respect to their differentiation potential and, as a consequence, the success of transplantation. In contrast, this potential is reduced when separately culturing the anulus fibrosus and nucleus pulposus cells, and some intervertebral disk-specific markers will not be expressed following transfer into the three-dimensional environment. For this reason, it is only mixed cultures that are particularly suitable in building up intervertebral disk tissue after transplantation in a degenerate intervertebral disk.

In addition, the cell and tissue transplants produced in vitro should not induce any immunologic reactions in the organism containing the transplant. Surprisingly, it was found that the cells and tissues produced in an autologous manner according to the invention do not induce any immunologic reactions.

The affected intervertebral disk tissue collected from the patient can be further processed in various ways:
(a) The intervertebral disk mixed cells are isolated from the biopsies according to conventional methods, using enzymatic digestion of the tissue, migration, or reagents recognizing the target cells. Adding autologous serum only, without addition of exogenous growth-promoting compounds and without addition of antibiotics, the above cells are cultured in cell culture vessels in conventional culture medium until a sufficient amount of cells is available (FIG. 2). This period of time is made as short as possible so as to avoid changes in their phenotypic properties. After sufficient cell propagation, the cells are harvested, and the cell transplant consisting of an intervertebral disk cell suspension is ready for therapeutic applications.

According to the invention, the isolated intervertebral disk cells are used in mixture, i.e., the cells are not separated according to anulus fibrosus and nucleus pulposus cells—tissue portions of which are included in the prolapsed intervertebral disk tissue—and cultured separately or as single-type cells. It is precisely these mixture conditions that later achieve improved intervertebral disk-specific differentiation of the cells (see FIG. 3). Hence, the above autologous mixed culturing technique for growing intervertebral disk cells —following transfer thereof into a three-dimensional environment —allows intervertebral disk-specific differentiation of the thus-cultured cells for the first time.

(b) In another method the isolated intervertebral disk cells are pre-cultured and briefly grown without passaging. Thereafter, the pre-cultured cells are harvested, frozen, and stored in deep-frozen state until used in transplantation. Prior to transplantation, the cells are thawed and cultured further together with autologous serum in conventional cell culture medium until a sufficient number of cells is reached. Following sufficient propagation of the cells, the cells are harvested, thus providing the cell transplant consisting of an intervertebral disk cell suspension. Surprisingly, it was noted that the intervertebral disk cells do not lose their specific properties with respect to the synthesis of specific marker and matrix proteins as a result of such freezing and thawing (see FIG. 5).

(c) Another preferred procedure likewise utilizes patient-derived affected intervertebral disk tissue as starting material. The tissue-building cells are isolated from the biopsies from anulus fibrosus and nucleus pulposus according to conventional methods, using enzymatic digestion of the tissue, migration, or reagents recognizing the target cells. Thereafter, these mixed cells are initially cultured in monolayer under autologous conditions, using a standard culture medium, until a sufficient number of cells is reached, subsequently transferred into cell culture vessels with hydrophobic surface and tapering bottom and cultured in suspension therein until a three-dimensional cell aggregate is formed which includes at least 40% by volume, preferably at least 60% by volume, and up to a maximum of 99% by volume of de novo-synthesized extracellular matrix (ECM) having differentiated cells embedded therein. By taking small samples, these values can be determined by a person skilled in the art. The cell aggregate having formed has an outer region wherein cells capable of proliferation and migration are present (see FIG. 1).

According to the invention, the isolated intervertebral disk cells are used in mixture, i.e., the cells are not separated according to anulus fibrosus and nucleus pulposus cells and cultured separately or as single-type cells. It is precisely under such mixture conditions that intervertebral disk-specific differentiation of the mixed cells is promoted in the three-dimensional culture and, as a consequence, in the formation of three-dimensional intervertebral disk tissue, and the expression of intervertebral disk-specific markers can only be achieved in such cultures, with formation of three-dimensional intervertebral disk tissue being promoted when using said mixed cultures (see FIG. 3). Hence, the above autologous mixed culturing technique permits production and use of an intervertebral disk-specific tissue transplant for the first time, which transplant is produced in an autologous fashion from degenerate, prolapsed intervertebral disk tissue.

The intervertebral disk mixed cells isolated from affected intervertebral disk tissue and used to produce autologous three-dimensional intervertebral disk cell aggregates such that the collected cells are integrated in a de novo-synthesized tissue survive even after a prolonged time of culturing, i.e., the cells inside the aggregates do not die. With increasing culturing time, the cells inside the aggregates undergo differentiation to form intervertebral disk cartilage tissue consisting of ECM, differentiated cells and a peripheral proliferation zone (see FIG. 1). During differentiation in the autologous cell culture, the spacing between the aggregated cells steadily increases due to formation of tissue-specific matrix (see FIG. 3, comparison of (3c) with (3d)). A tissue histology develops inside the intervertebral disk tissue produced in vitro, which is highly similar to natural tissue. During the further course of production of intervertebral disk cartilage tissue, a "proliferation zone" is formed at the boundary thereof. This zone is invaluably advantageous in that, following incorporation of the thus-formed intervertebral disk cartilage tissue in degenerate intervertebral disks, the cells situated in this peripheral zone are capable of migrating to make active contact with the surrounding tissue and/or enable integration of the in vitro produced intervertebral disk cartilage tissue in the environment thereof. Thus, the tissue-specific cell aggregates produced are excellently suited for use in the treatment of degenerate intervertebral disks and in in vivo neogenesis of intervertebral disk tissue.

In view of the biomechanical strain on the intervertebral disks immediately after treatment, and with respect to the target of restoring the intervertebral disk in its height at the same time with transplanting the intervertebral disk cartilage tissue, it can be advantageous to transplant larger pieces of tissue at an early stage. In this event, at least two, or preferably more of the intervertebral disk cartilage tissues obtained in vitro are fused by continuing culturing thereof under the same conditions and in the same culture vessels as described above until the desired size is reached (see also FIG. 4).

A medium usual for both suspension and monolayer culture, e.g. Dulbecco's MEM, with addition of serum, can be used as cell culture medium. It is preferred to use DMEM and HAMS at a ratio of 1:1. However, to avoid immunologic response in the patient to the tissue produced in vitro, it is preferred to use autologous serum from the patient as serum. It is also possible to use xenogenic or allogenic serum.

According to the invention, no antibiotic, fungistatic agents or other auxiliary substances are added to the culture medium. It has been found that only autologous or allogenic culturing of the cells and cell aggregates and culturing with no antibiotic and fungistatic agents allows non-affected proliferation and differentiation of the cells in the monolayer culture and undisturbed formation of the specific matrix within the cell aggregates. Furthermore, by avoiding additives during the production, any immunologic reaction is excluded when incorporating the tissue produced in vitro in a human or animal organism.

The size of the intervertebral disk tissue produced depends on the number of incorporated cells per volume of culture medium. For example, when incorporating $1 \times 10^7$ cells in 300 µl of culture medium, three-dimensional intervertebral disk cell aggregates about 500-700 µm in diameter are formed within one week. Another option would be in vitro fusion of small cell aggregates to form larger ones—as described above—and incorporation of the latter in the intervertebral disk. According to the invention, it is preferred to use between $1\times10^4$ and $1\times10^7$ cells in 300 µl of culture medium to produce small cell aggregates, more preferably $1\times10^5$ cells. Depending on the cell type and patient-specific characteristics, the intervertebral disk tissues having formed in vitro after several days are then cultured in a suitable culture medium for at least 2-4 weeks to induce formation of the tissue-specific matrix. From about one week of culturing on, it is possible in special cases to fuse individual in vitro intervertebral disk tissues so as to increase the size of the tissue patch.

As cell culture vessels for the inventive culturing in suspension, those having a hydrophobic, i.e., adhesion-preventing surface, such as polystyrene or Teflon, can preferably be used. Cell culture vessels with a non-hydrophobic surface can be hydrophobized by coating with agar or agarose. Further additives are not required. Preferably, well plates are used as cell culture vessels. For example, 96-well plates can be used to produce small cell aggregates, and 24-well plates to produce said fused aggregates.

The invention is also directed to a surgical technique of transplanting the intervertebral disk cells and the in vitro-produced three-dimensional intervertebral disk cartilage tissues into a damaged intervertebral disk. According to the invention, transplantation is effected by injecting the intervertebral disk cells under fluoroscopic control, following disinfection of the skin, sterile covering of the skin area and local anesthesia, and—in a preferred fashion—strictly avoiding the use of contrast media.

To this end, the intervertebral disk cell transplants—following production in a laboratory—are filled in special transportation tubes with tapering bottom, rounded or sharp, and—in the operating room—drawn up in a syringe through a puncture needle with e.g. a slant-ended cannula. Complete uptake of the solution containing the cells is made possible especially by the tapering bottom of the transportation vessel and the slant-ended cannula. To ensure delivery of the cells in the intervertebral disk without damaging the cells and with lowest possible loss of liquid, i.e. cells, the puncture needle essentially has an inner diameter of 0.4 to 2 mm. According to the present invention, transplantation by injecting the intervertebral disk cells in the intervertebral disk to be treated is effected particularly at the side opposite to the previously operated side of the intervertebral disk (removal of intervertebral disk prolapse), using a slant-ended puncture needle. According to the invention, injection of the cell transplant takes place under fluoroscopic control because the actual delivery of cells into the intervertebral disk interior must be monitored. Conventionally, the use of contrast media is possible which, however, damage the cells, thereby preventing successful cell transplantation. Following delivery of the intervertebral disk cells in the intervertebral disk space, the puncture needle is retracted from the intervertebral disk. Preferably, the patient then is ordered to strict bed rest for 12 hours, followed by 12-24 hours of regular bed rest and 24-48 hours bed rest with physiotherapeutic exercises. Thereafter, the vertebral column is stabilized e.g. for some weeks using a conventional suitable orthesis.

As in the case of intervertebral disk cells, transplantation of the three-dimensional in vitro-produced intervertebral disk cartilage transplants is effected by means of a puncture needle, in particular. To make sure that mechanical and therefore biological damage of the intervertebral disk cartilage transplants is avoided during injection, a puncture needle with a diameter of at least 500 µm is used. According to the invention, essentially single passage through the puncture needle is effected to avoid mechanical damage of the intervertebral disk cartilage transplants. For this reason, the intervertebral disk cartilage transplants are transferred in a syringe following production thereof in a laboratory, on which syringe the puncture needle merely has to be placed in the operating room. According to the invention, the puncture needle used in this case must also have a slanted opening so as to allow rapid delivery—by virtue of the enlarged area of delivery—of the intervertebral disk cartilage transplants in a smallest possible liquid volume (delivery volume). Thereafter, injection is effected as described for the cell transplants above.

The invention is also directed to therapeutic formulations comprising the intervertebral disk cell transplants and intervertebral disk cartilage tissue of the invention, e.g. injection solutions.

The invention is also directed to the use of the intervertebral disk cartilage tissues of the invention in testing active substances which e.g. have influence on the formation and differentiation of matrix and cells. To this end, the intervertebral disk cell aggregates are produced in accordance with the invention, medications to be tested are added at varying stages of maturing, and a variety of parameters of in vitro intervertebral disk tissue production and maturing are characterized. Compared to conventional testing of drugs in animals or tumor cell systems, these tests are patient-specific owing to the use of autologous material only and allow individual diagnosis.

Without intending to be limiting, the invention will be illustrated in more detail with reference to the examples.

EXAMPLES

Example 1
Production of Intervertebral Disk Cell Transplants

Intervertebral disk cartilage cells from anulus fibrosus and nucleus pulposus are isolated from affected intervertebral disk tissue, using enzymatic digestion by incubation with collagenase solution. Following separation of the isolated cells from undigested cartilage tissue, the cells in the form of a mixed-cell population are transferred in cell culture flasks and, following addition of DMEM/HAMS F12 culture medium (1/1) and 10% autologous serum from the patient, incubated at 37° C. and 5% $CO_2$. The medium is exchanged twice a week. After reaching the confluent stage, the cell layer is washed with physiological saline solution and harvested from the cell culture surface using trypsin. After another wash, the intervertebral disk cells are transferred in physiological saline solution and provided for transplantation.

The differentiation potential of the intervertebral disk cells included in the cell transplant was demonstrated in an in vitro model. Intervertebral disk-specific matrix proteins and marker proteins are expressed (FIG. 3) and a intervertebral disk-specific tissue formed in this way.

Example 2
Transplantation of Intervertebral Disk Cartilage Cells

The intervertebral disk cell transplants produced in Example 1 (minimum: 1,000 cells, maximum: 100 million cells), preferably about 1 million intervertebral disk cartilage cells, were taken up in physiological saline solution and injected in an affected intervertebral disk. It was noted, among other things, that the water content was rising and the height of the intervertebral space was maintained in the treated intervertebral disk, both of the above being due to the matrix proteins synthesized by the intervertebral disk cartilage cells.

The in vitro-produced intervertebral disk cell transplants of the invention are accepted by patients, ensure rapid integration of the cells capable of proliferation and migration, as well as regeneration of the intervertebral disk tissue as a result of the differentiating ability of the cells included therein. Therefore, the intervertebral disk cell transplants allow rapid re-development of intervertebral disk tissue, rapid convalescence of patients, and restoration of the intervertebral disk function.

Example 3

In vitro Production of Intervertebral Disk Cartilage Tissue

Intervertebral disk cartilage cells from anulus fibrosus and nucleus pulposus are isolated from prolapsed intervertebral disk tissue, using enzymatic digestion by incubation with collagenase solution. Following separation of the isolated cells from undigested tissue, the cells in the form of a mixed culture are transferred in cell culture flasks and, following addition of DMEM/HAMS F12 culture medium (1/1) and 10% autologous serum from the patient, incubated at 37° C. and 5% $CO_2$. The medium is exchanged twice a week. After reaching the confluent stage, the cell layer is washed with physiological saline solution and harvested from the cell culture surface using trypsin. After another wash, $1 \times 10^5$ cells each time are transferred in a cell culture vessel coated with agarose. After one day, the first cells have arranged into aggregates. These aggregates are supplied with fresh medium at regular intervals and cultured for at least 2 weeks.

The structure of the resulting intervertebral disk cartilage tissue is represented in the microscopic image in FIG. 1 which shows the cross-section of an intervertebral disk tissue produced according to the invention, with ECM as a zone of reduced proliferation and formation of tissue-specific matrix proteins and P as outer proliferation zone.

Expression and deposition of intervertebral disk-specific matrix components and regulatory proteins such as aggrecan (FIG. 3a), hyaline-specific proteoglycans (FIG. 3b), collagen type I (FIG. 3c), collagen type II (FIG. 3d) and collagen type III (FIG. 3e) was detected in the above in vitro intervertebral disk tissues. These are components of native intervertebral disk cartilage tissue in vivo, representing the most important structural proteins which are of crucial importance for the function of intervertebral disk cartilage.

Surprisingly, when cultured as a mixture of anulus fibrosus and nucleus pulposus, the intervertebral disk cells isolated from affected intervertebral disk tissue show high proliferation capacity (FIG. 2) and very high differentiation potential for the formation of intervertebral disk-specific matrix proteins and regulatory proteins (see also FIG. 3), and their properties can be retained by the procedure of freezing and thawing (see also FIG. 5).

Example 4

Transplantation of Intervertebral Disk Cartilage Tissue

The intervertebral disk cartilage tissue produced in Example 3 (about 10 to 1000 tissue patches, each comprising $1 \times 10^5$ cells), preferably 100 tissue patches, in physiological saline solution was taken up in a syringe in the laboratory and injected into the intervertebral space of affected or damaged intervertebral disks using a puncture needle with slanted opening. The intervertebral disk cartilage tissue produced in vitro according to the invention is well-accepted by patients and, in addition to realizing the mechanical function of the tissue produced, ensures rapid integration of the resulting tissue patch in the outer layers of the aggregate by the cells capable of proliferation and migration, as well as regeneration of the intervertebral disk tissue as a result of the differentiating ability of the cells included therein. Hence, structure and function of the tissue patches allow rapid re-development of intervertebral disk tissue, rapid convalescence of patients, and restoration of the intervertebral disk function.

FIG. 4 shows five intervertebral disk tissues undergoing fusion. As can be seen, the tissue spheres adhere to each other, and coalesce, so to speak, the boundary between any two intervertebral disk tissues is no longer recognizable. After a prolonged period of culturing, the intervertebral disk tissues undergo complete fusion to form a larger in vitro tissue patch. The structure of the larger cell aggregates thus obtained is comparable with in vitro intervertebral disk tissue. They can include up to maximum of 99% ECM, and the resulting cells are vital.

The invention claimed is:

1. A method for the production of autologous intervertebral disk cell transplants,
   wherein vital intervertebral disk cells are isolated from at least one of degenerate prolapsed intervertebral disk tissue and affected intervertebral disk tissue wherein anulus fibrosus cells and nucleus pulposus cells so isolated are cultured as a mixture of these cells in a monolayer with addition of autologous serum without addition of exogenic growth-promoting compounds and without addition of antibiotics and fungistatic agents, thereby obtaining intervertebral disk cell transplants having cells which are capable of proliferation, migration and differentiation.

2. The method according to claim 1, wherein during growth, the intervertebral disk cells isolated from said degenerate prolapsed intervertebral disk tissue are cultured in a cell culture medium including 1-20% of added autologous serum, wherein the cell culture medium has a ratio of alpha-MEM medium and HAM-F12 medium which is between 2:1 and 1:2, at 36.8-37° C. in air containing 5% carbon dioxide and said air having a humidity of 85-95%.

3. The method according to claim 1, wherein the isolated intervertebral disk cells, following growth thereof in monolayer, are frozen in a solution of 10% DMSO, 20% serum and 70% culture medium, followed by thawing, so that their properties with respect to the synthesis of specific matrix components and markers remain unchanged and tissue structures consisting of intervertebral disk-specific matrix proteins are formed in vitro and in vivo.

4. A method for the production of intervertebral disk tissue transplants, wherein the intervertebral disk cell transplants produced according to claim 1 are cultured with addition of autologous serum in a culture vessel with hydrophobic surface and tapering bottom, thereby obtaining three-dimensional intervertebral disk tissue transplants having an extracellular matrix, and a peripheral proliferation zone.

5. The method according to claim 4, wherein the isolated intervertebral disk cells, following growth thereof in monolayer, are cultured in a cell culture medium including 1-20% of added autologous serum, wherein the cell culture medium has a ratio of alpha-MEM medium and HAM-F 12 medium which is between 2:1 and 1:2, at 36.8-37° C. in air containing 5% carbon dioxide and said air having a humidity of 85-95%, thereby becoming capable of differentiating, forming matrix structures comprising specific intervertebral disk matrix proteins.

* * * * *